United States Patent [19]

Mark et al.

[11] Patent Number: 4,677,064
[45] Date of Patent: Jun. 30, 1987

[54] HUMAN TUMOR NECROSIS FACTOR

[75] Inventors: David F. Mark, Danville; Alice M. Wang, Walnut Creek; Martha B. Ladner, Richmond; Abla A. Creasey, Piedmont; Janelle N. Van Arsdell, Richmond; Leo S. Lin, Fremont, all of Calif.

[73] Assignee: Cetus Corporation, Emeryville, Calif.

[21] Appl. No.: 730,696

[22] Filed: May 2, 1985

Related U.S. Application Data

[63] Continuation-in-part of Ser. No. 670,360, Nov. 9, 1984, which is a continuation-in-part of Ser. No. 661,026, Oct. 10, 1984, abandoned.

[51] Int. Cl.$^4$ .................... C12P 21/00; C12N 15/00; C12N 1/00; A61K 39/00
[52] U.S. Cl. .................... 435/68; 435/172.3; 435/253; 435/317; 514/8; 514/12; 530/350; 530/351; 530/395; 530/808; 424/85; 424/88; 536/27
[58] Field of Search .................. 435/68, 70, 240, 243, 435/253, 172.3, 317; 514/12, 8; 260/112.5 R; 935/9, 11-13, 65; 536/27; 424/88, 85; 530/350, 351, 352, 395, 808

[56] References Cited

U.S. PATENT DOCUMENTS 4,399,216 8/1983 Axel et al. .................... 435/172.3
4,447,355 5/1984 Sakamoto et al. .............. 260/112 B
4,457,916 7/1984 Hayashi et al. ................ 424/10 R
4,495,282 1/1985 Ohnishi et al. ................ 435/68

FOREIGN PATENT DOCUMENTS 0100641 7/1983 European Pat. Off. .......... 435/68
2106117 4/1983 United Kingdom ............ 260/112 B

OTHER PUBLICATIONS

Haidaris et al., *Infec. and Immun.*, 1983, vol. 42, pp. 385–393.
Pennica, D. et al., *Nature*, vol. 312, Dec. 27, 1984, pp. 724–729.
Shirai et al., *Nature*, vol. 313, Feb. 28, 1985.
Wang et al., *Science*, vol. 22, Apr. 12, 1985, pp. 149–157.
Carswell, E. A. et al., *PNAS*, 1975, vol. 72, pp. 3666–3670.
Mannel, D. N. et al., *Infec and Immun*, 1980, vol. 30, pp. 523–530.
Matthews, *Brit J. Cancer*, 1981, vol. 44, pp. 418–423.
Mannel et al., *Infec and Immun*, 1983, vol. 42, pp. 385–393.
Williamson et al., *PNAS*, vol. 80, pp. 5397–5401, Sep. 1983, "Human Tumor Necrosis Factor Produced by Human B-Cell Lines Synergistic Cytototic Interaction With Human Interferon".
Banerji et al., *Cell*, vol. 27, pp. 299–308, 1981, "Expression of a β-Globin Gene is Enhanced by Remote SV40 DNA Sequences".
Wasylyk et al., *Cell*, vol. 32, pp. 503–514, Feb. 1983, "The SV40 72 Bp Repeat Preferentially Potentiates Transcription Starting From Proximal Natural or Substitute Promotor Elements".
Shimitake et al., *Nature*, vol. 292, Jul. 9, 1981, "Purified & Regulatory Protein C II Positively Activator Promotors for Lysogenic Development".
Goeddel et al., *Nucleic Acids Research*, vol. 8(18) 1980, "Synthesis of Human Fibroblast Interferon by *E. Coli*".

*Primary Examiner*—Thomas G. Wiseman
*Assistant Examiner*—Robin Teskin
*Attorney, Agent, or Firm*—Albert P. Halluin; Kate H. Murashige

[57] ABSTRACT

Human Tumor necrosis factor (TNF) has been prepared using recombinant methods. A human promyelocytic leukemia cell line has been induced using an improved induction procedure, and the TNF purified to homogeneity. Methods, vectors, and cells useful in obtaining human TNF in practical amounts are disclosed. Muteins having N-terminal deletions, which muteins have superior biological activity, are also disclosed.

14 Claims, 2 Drawing Figures

1 CACACCCTGACAAGCTGCCAGGCAGGTTCTCTTCCTCTCACATACTGACCCACGGCTCCA

61 CCCTCTCTCCCCTGGAAAGGACACCATGAGCACTGAAAGCATGATCCGGGACGTGGAGCT
                        METSerThrGluSerMETIleArgAspValGluLeu

121 GGCCGAGGAGGCGCTCCCCAAGAAGACAGGGGGGCCCCAGGGCTCCAGGCGGTGCTTGTT
    AlaGluGluAlaLeuProLysLysThrGlyGlyProGlnGlySerArgArgCysLeuPhe

181 CCTCAGCCTCTTCTCCTTCCTGATCGTGGCAGGCGCCACCACGCTCTTCTGCCTGCTGCA
    LeuSerLeuPheSerPheLeuIleValAlaGlyAlaThrThrLeuPheCysLeuLeuHis

241 CTTTGGAGTGATCGGCCCCCAGAGGGAAGAGTCCCCCAGGGACCTCTCTCTAATCAGCCC
    PheGlyValIleGlyProGlnArgGluGluSerProArgAspLeuSerLeuIleSerPro

301 TCTGGCCCAGGCAGTCAGATCATCTTCTCGAACCCCGAGTGACAAGCCTGTAGCCCATGT
    LeuAlaGlnAlaValArgSerSerSerArgThrProSerAspLysProValAlaHisVal
      1           6           11          16

361 TGTAGCAAACCCTCAAGCTGAGGGGCAGCTCCAGTGGCTGAACCGCCGGGCCAATGCCCT
    ValAlaAsnProGlnAlaGluGlyGlnLeuGlnTrpLeuAsnArgArgAlaAsnAlaLeu
        21          26          31          36

421 CCTGGCCAATGGCGTGGAGCTGAGAGATAACCAGCTGGTGGTGCCATCAGAGGGCCTGTA
    LeuAlaAsnGlyValGluLeuArgAspAsnGlnLeuValValProSerGluGlyLeuTyr
        41          46          51          56

481 CCTCATCTACTCCCAGGTCCTCTTCAAGGGCCAAGGCTGCCCCTCCACCCATGTGCTCCT
    LeuIleTyrSerGlnValLeuPheLysGlyGlnGlyCysProSerThrHisValLeuLeu
        61          66          71          76

541 CACCCACACCATCAGCCGCATCGCCGTCTCCTACCAGACCAAGGTCAACCTCCTCTCTGC
    ThrHisThrIleSerArgIleAlaValSerTyrGlnThrLysValAsnLeuLeuSerAla
        81          86          91          96

601 CATCAAGAGCCCCTGCCAGAGGGAGACCCCAGAGGGGGCTGAGGCCAAGCCCTGGTATGA
    IleLysSerProCysGlnArgGluThrProGluGlyAlaGluAlaLysProTrpTyrGlu
        101         106         111         116

661 GCCCATCTATCTGGGAGGGGTCTTCCAGCTGGAGAAGGGTGACCGACTCAGCGCTGAGAT
    ProIleTyrLeuGlyGlyValPheGlnLeuGluLysGlyAspArgLeuSerAlaGluIle
        121         126         131         136

721 CAATCGGCCCGACTATCTCGACTTTGCCGAGTCTGGGCAGGTCTACTTTGGGATCATTGC
    AsnArgProAspTyrLeuAspPheAlaGluSerGlyGlnValTyrPheGlyIleIleAla
        141         146         151         156

781 CCTGTGAGGAGGACGAACATCCAACCTTCCCAAACGCCTCCCCTGCCCAATCCCTTTAT
    Leu...

841 TACCCCTCCTTCAGACACCCTCAACCTCTTCTGGCTCAAAAAGAGAATTGGGGGCTTAG

901 GGTCGGAACCCAAGCTTAGAACTTTAAGCAACAAGACCACCACTTCGAAACCTGGGATTC

961 AGGAATGTGTGGCCTGCACAGTGAAGTGCTGGCAACCACTAAGAATTCAAACTGGGGCCT

1021 CCAGAACTCACTGGGGCCTACAGCTTTGATCCCTGACATCTGGAATCTGGAGACCAGGGA

1081 GCCTTTGGTTCTGGCCAGAATGCTGCAGGACTTGAGAAGACCTCACCTAGAAATTGACAC

1141 AAGTGGACCTTAGGCCTTCCTCTCTCCAGATGTTTCCAGACTTCCTTGAGACACGGAGCC

1201 CAGCCCTCCCCATGGAGCCAGCTCCCTCTATTTATGTTTGCACTTGTGATTATTTATTAT

1261 TTATTTATTATTTATTTATTTACAGATGAATGTATTTATTTGGGAGACCGGGGTATCCTG

1321 GGGGACCCAATGTAGGAGCTGCCTTGGCTCAGACATGTTTTCCGTGAAAACGGAGGCTGA

1381 ACAATAGGCTGTTCCCATGTAGCCCCCTGGCCTCTGTGCCTTCTTTTGATTATGTTTTTT

1441 AAAATATTATCTGATTAAGTTGTCTAAACAATGCTGATTTGGTGACCAACTGTCACTCAT

1501 TGCTGAGGCCTCTGCTCCCCAGGGAGTTGTGTCTGTAATCGGCCTACTATTCAGTGGCGA

1561 GAAATAAAGGTTGCTTAGGAAAGAA

HUMAN TUMOR NECROSIS FACTOR

CROSS-REFERENCE TO RELATED APPLICATIONS

This is a continuation-in-part of U.S. Ser. No. 670,360, filed Nov. 9, 1984 which is a continuation-in-part of U.S. Ser. No. 661,026, filed Oct. 10, 1984, now abandoned). It further relates to subject matter disclosed in U.S. Ser. No. 698,939, filed Feb. 7, 1985.

TECHNICAL FIELD

This invention relates to the recombinant production of human protein factors. In particular, it concerns production of a protein which is selectively toxic to tumors, and to muteins thereof which are improved in specific activity.

BACKGROUND ART

A factor which became familiar as tumor necrosis factor (TNF) was first encountered by Carswell, et al, *Proc Natl Acad Sci* (USA) (1975) 72:3666. It was found that the sera of endotoxin treated mice, rabbits, or rats which had been previously sensitized with an immunopotentiator such as Bacillus Calmette-Gurin (BCG) contained a substance which, when injected into mice harboring transplanted tumors, caused extensive hemorrhaging of the tumors, without undesirable side effects on the recipient. The sera were thus presumed to contain a substance which was selectively necrotic to tumor cells, and neutral with respect to its reactions with normal tissue, hence the designation, TNF. The ability to cause this selective tumor destruction when injected into whole animals became a standard in vivo assay defining TNF.

TNF has also been produced in cell culture. Matthews, et al, *Brit J Cancer* (1981) 44:418 were able to obtain TNF activity in the medium of mononuclear phagocytes derived from BCG-injected rabbits; Mannel, et al, *Infect Immun* (1980) 30:523; ibid (1981) 33:156 obtained TNF activity from the medium of macrophage-enriched peritoneal exudate cells from BCG-infected mice after the cell culture was induced with endotoxin.

Attempts have been made to purify whatever factor is responsible for the selective cytotoxicity against neoplastic cells but, because the substances are apparently present only in tiny amounts either in the serum of whole animals or in tissue culture media, it has not been possible to effect complete purification. Furthermore, the protein or proteins are evidently unstable, and two recent U.S. patents, Nos. 4,447,355 and 4,457,916 are directed to methods for stabilizing the activity of the preparation by addition of, for example, albumin or a carbohydrate material. In the procedures of those disclosures, using standard purification procedures developed by others, it was possible to obtain a specific activity for preparations of TNF to approximately $1 \times 10^6$ units/mg, where units were defined in terms of an in vitro assay for cytotoxicity against murine L-M cells (ATCC CCL 1.2). It has not been possible, however, to obtain material which is both active in the in vivo (Carswell) tumor necrosis assay for TNF and of sufficient purity to permit amino acid sequence information to be obtained.

Indeed, because of the unavailability of pure cytotoxic protein, it is unclear at present how many proteins may be available which are selectively necrotic to cancer cells. The in vivo method of Carswell, et al (supra) has been accepted as the standard defining TNF. Because of the cross species activity of these factors, this assay is, in one sense, conveniently diagnostic. However, the more conveniently performed in vitro assay for cytotoxicity has frequently been used as an index of TNF activity, despite considerable confusion about whether there exists a one-to-one correlation between the in vitro assay and the test defining TNF. Indeed, a protein derived from a transformed B-cell line, which is active in the in vitro assay, has been designated "lymphotoxin", purified to homogeneity and partially sequenced (Genentech, EPO Patent Publication 0100641, published Feb. 15, 1984). It has been assumed that lymphotoxin is a different protein from "TNF" because it is of non-macrophagic origin. Further, anti-sera prepared agasint lymphotoxin do not cross react with the cytotoxic (TNF) factor purified from macrophage (Stone-Wolff, D., et al, *J Exp Med* (1984) 159:828.

Provision of a defined protein sequence which is capable of a cytotoxic effect specifically directed against tumor cells would, of course, represent a major benefit for both diagnosis and therapy of malignant diseases. It appears, also, that certain of these factors may exhibit anti-parasitic activity; it has been shown that a protein designated TNF, derived from sera of BCG injected mice, exhibits cytotoxic affects on malaria parasites (*Plasmodium falciparum*)) in vivo and in vitro (Haidans, et al, *Infect Immun* (1983) 42:385).

DISCLOSURE OF THE INVENTION

It has now been shown that a human promyelocytic leukemia cell line (HL-60, ATCC No. CCL 240), when appropriately induced, produces a tumor necrosis factor in significant amounts. This factor has been purified, sequenced, and produced using recombinant techniques. Thus, there is, for the first time, a chemically defined factor which is selectively cytotoxic against human tumor cells. This represents opportunities to provide significant amounts of the material for use in therapy, to make programmed modifications to improve activity, and to design suitable diagnostic tests to detect the presence of tumors in an organism, i.e., the availability of a recombinant source for this protein represents the attainment of feasibility for manipulating this useful peptide for therapy and for diagnosis. While at least one form of TNF is presumably natively produced by humans in response to tumor formation, without the flexibility and the quality and quantity assurance conferred by recombinant production, no means were available for taking advantage of its properties.

Thus, in one aspect, the invention relates to recombinant human TNF. In other aspects, it relates to an uninterrupted DNA sequence encoding this protein, to sequences capable of effecting its expression, to transformation vectors capable of conferring on a transformant host the ability to express TNF, the recombinant hosts so transformed, and to methods of obtaining the various compositions of the invention.

In other aspects, the invention relates to a protein of the amino acid sequence encoded by the DNA sequence set forth in FIG. 1 herein, specifically in glycosylated and non-glycosylated forms.

The invention also relates to several specific recombinant mutein forms of TNF containing alterations in primary structure as compared to that shown in FIG. 1, and to methods and materials for their production.

These muteins are comparably or more active in their capacity to kill tumor cells selectively than is the TNF of the primary sequence shown in FIG. 1 (mTNF). These muteins include corresponding proteins leaving deletions of 1–10 N-terminal amino acid residues and cysteine depleted muteins wherein 1–10 of the N-terminal amino acids are not present.

The invention further relates to a protein of the N-terminal sequence:

Val-Arg-Ser-Arg-Thr-Pro-Ser-Asp-Lys-Pro-Val-
 Ala-Val-Ser-Val-Ala-Asn-Pro-(Gln)-(Ala)-Glu-
 Gly and to improved methods for inducing the production of, and purifying this amino acid sequence from, promyelocytic leukemia cells. The invention also relates to pharmaceutical compositions containing TNF, to methods of treatment using these compositions, and to an improved assay method for TNF.

BRIEF DESCRIPTION OF THE DRAWINGS

FIG. 1 shows the complete nucleotide sequence of pE4 and the deduced amino acid sequence for human TNF.

MODES OF CARRYING OUT THE INVENTION

A. Definitions

As used herein, "tumor necrosis factor" (TNF) refers to an amino acid sequence substantially equivalent to that shown in FIG. 1, which is capable of selective cytotoxicity against tumor cells. The amino acid sequence, to fit the definition herein, must be active in the in vitro cytotoxicity assay based on the continuous murine connective tissue cell line L-929 as described hereinbelow. It is recognized that this definition of TNF activity is not precisely the same as that set forth in the disclosure coining this term by Carswell, et al (supra). However, the activity as confirmed by the in vitro cytotoxicity assay against human tumor cells provides sufficient assurance of utility that qualification as a tumor necrosis factor using this assay is justified. As set forth hereinbelow, the cytotoxicity against L-929 appears to generalize to other human tumors. It is expected that there is a substantial overlap between factors active in the specified cytotoxicity assay and the in vivo assay outlined by Carswell.

The TNF protein of the invention, depending on the pH of its environment, if suspended or in solution, or of its environment when crystallized or precipitated, if in solid form, may be in the form of pharmaceutically acceptable salts or may be in neutral form. The free amino groups of the protein are, of course, capable of forming acid addition salts with, for example, inorganic acids such as hydrochloric, phosphoric, or sulfuric acid; or with organic acids such as, for example, acetic, glycolic, succinic, or mandelic acid. The free carboxyl groups are capable of forming salts with bases, including inorganic bases such as sodium, potassium, or calcium hydroxides, and such organic bases as piperidine, glucosamine, trimethylamine, choline, and caffeine. In addition, the protein may be modified by combination with other biological materials such as lipids and saccharides, or by side chain modification such as acetylation of amino groups, phosphorylation of hydroxyl side chains, or oxidation of sulfhydryl groups. All of these modifications are included within the scope of the definition, so long as the TNF activity is retained.

Finally, it is understood that minor modifications of primary amino acid sequence may result in proteins which have substantially equivalent or enhanced activity as compared to the sequence set forth in FIG. 1. These modifications may be deliberate, as through site-directed mutagenesis, or may be accidental such as through mutation in hosts which are TNF producers. All of these modifications are included as long as TNF activity, as above-defined, is retained.

In particular, it has been found, and is illustrated below, that the mutein lacking the first four amino acids at the N-terminus of the sequence shown in FIG. 1 (Val-Arg-Ser-Ser) has a specific activity several fold higher than the TNF of the structure shown. Accordingly, the definition of TNF specifically includes this truncated form. In addition, muteins lacking the N-terminal ten or less amino acids have similarly enhanced activity. It thus generally appears that deletions of up to 10 amino acids from the N-terminus do not destroy, but, in fact, enhance biological activity.

Therefore, the definition of TNF herein specifically includes proteins having an amino acid sequence substantially equivalent to that shown in FIG. 1, but lacking 1–10 of the amino acids at the N-terminal sequence as shown in that figure. It should be noted that Shirai, T., et al, Nature (1985) 313:803–806 produced a recombinant TNF using an expression vector constructed from DNA obtained from a human genomic bank. In the construct, the encoded protein lacks the first two amino acids of the N-terminal sequence shown in FIG. 1 herein. For reasons that are unclear, but which apparently relate to rabbit TNF genomic structure, Shirai, et al, assumed that the proper N-terminus began at the position shown herein as position 3 and constructed the vector accordingly. As a consequence, the Shirai-produced TNF has the N-terminal sequence Ser-Ser-Arg-Thr, etc. The TNF produced by Shirai was shown to have activity in vivo. Direct comparison of the activity of this protein with that of the recombinantly produced mTNF and TNF muteins herein is not at present available.

U.S. Ser. No. 698,939, filed Feb. 7, 1985, assigned to the herein assignee and incorporated herein by reference, discloses cysteine-depleted muteins of the mTNF of FIG. 1. In general, neutral amino acid replacements of the cysteine at position 69 result in active TNF proteins. These muteins can also be modified according to the method of the invention herein to obtain truncated forms which retain TNF activity and may have enhanced specific activity in vitro and in vivo. These muteins lack 1–10 amino acids at the N-terminus. These muteins, too, specifically fall within the definition of TNF.

As to notation, for convenience, the protein having the amino acid sequence numbered 1–157 in FIG. 1 will be used as a reference and designated, perhaps arbitrarily, mTNF (mature TNF). All other amino acid sequences having homology with mTNF and showing TNF biological activity will be referred to as "muteins" of mTNF and will be denoted as to their differences from mTNF using the numbering of residues shown in the figure. For example, muteins which have substitutions for cysteine at position 69 will be denoted using the substituted residue and the position number, e.g., peptides having a serine in place of the cysteine at position 69 are designated $ser_{69}$ TNF. Muteins which lack, for example, three N-terminal amino acids as compared to the protein shown in FIG. 1 will be designed ∇3TNF. Where both of the foregoing alterations are made, the mutein is designated ∇3ser₆₉TNF.

Not all muteins of mTNF are recombinantly or deliberately produced. Indeed, as will be noted by comparing the sequence obtained for the twenty-two N-terminal amino acids of the HL-60 secreted TNF, set forth in ¶ D.1.b below, with the corresponding portion of the deduced sequence set forth in FIG. 1, minor modifications appear in the primary structure although both proteins exhibit TNF activity. Specifically, the deduced sequence has an additional pair of serine residues following the serine at position 3 before resuming the homology shown between positions 4–12 of the HL-60 derived protein and positions 6–14 of the deduced sequence. In addition, positions 13 and 14 of the HL-60 derived protein are val-ser; the corresponding positions 15 and 16 of the deduced sequence are his-val.

"Operably linked" refers to a juxtaposition wherein the components are configured so as to perform their usual function. Thus, control sequences operably linked to coding sequences are capable of effecting the expression of the coding sequence.

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host used.

"Cells" or "recombinant host" or "host cells" are often used interchangably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

B. General Description

The methods illustrated below to obtain the DNA sequence encoding human TNF are illustrative and typical. Other approaches could have been, and may be used. As the entire DNA sequence has been obtained in intronless form, and is disclosed herein, it is, of course, not necessary to repeat this process to obtain the desired DNA sequence. Nor is it necessary to utilize the same systems for expression that are illustrated herein. As set forth in more detail in ¶ C a variety of hosts and control sequences are available in the art which could be used to effect production of the desired TNF.

In the illustrated process, the human promyelocytic leukenia cell line, HL-60 was induced using an improved induction procedure to secrete TNF protein as described in ¶ B.1. This protein was purified to homogeneity using a novel purification process as described in ¶ B.2, and the resulting purified protein subjected to amino acid sequence determination. This permitted the construction of probe mixtures, which were then used to obtain the appropriate coding sequences, as described in ¶ B.3. The coding sequences were used for expression in this illustration by ligation into vectors containing suitable procaryotic control systems, as well as utilizing viral promoters for expression in mammalian cells.

Modifications were made in the coding sequence in order to generate muteins of the DNA sequences which had been obtained from probing of a cDNA library. Such modifications were effected by primer directed mutagenesis, and generally resulted in shorter forms of the TNF which showed enhanced activity.

B.1. Improved Induction Procedure

The cell line subject to induction, the HL-60 human promyelocytic leukemia cell line, is itself relatively undifferentiated. If allowed to differentiate, it would produce colonies of more specifically defined cell types. Depending on subsequent events, it could mature into granulocytes, or into monocytes which could subsequently be further differentiated into macrophages. It has been assumed that the macrophage fraction is responsible for the in vivo production of TNF. The apparently closely related lymphotoxin, on the other hand, is thought to be produced by B lymphocyte cells.

It has been found that the level of TNF produced by subject cells can be increased by 10–20 fold by an improvement in the induction procedure. The known procedure, devised by Gifford, G., et al, (personal communication), uses treatment with the phorbol ester 12-O-tetradecanoylphorbol-13-acetate (TPA) at 10 µg/ml for 30 min at 37° C. in 20% serum. The cell cultures are then spun down, and treated with the endotoxin at 10 µg/ml in serum-free medium supplemented with transferrin and insulin (10 µg/ml each). By lowering the concentration of the phorbol ester to 100 ng/ml in the initial incubation using serum-free medium, and by the addition of 10 µM calcium ionophore A23817 at the endotoxin treatment step, the content of TNF in the supernatant after induction with the endoxoxin is substantially increased.

B.2. Purification of TNF

Also disclosed is an improved method for purifying TNF from induced cell cultures. This method comprises treating the supernatant containing TNF with an anion exchange resin under conditions which do not permit the adsorption of the TNF, followed by treating the TNF containing-fractions with a sizing gel, to obtain active fractions which are then subjected to SDS PAGE. The TNF containing fraction from SDS-PAGE is further purified using HPLC.

In the first step, the supernatant containing TNF is optionally concentrated before application to the anion exchange resin, such as by treatment with a commercially available concentrating filter such as an Amicon hollow fiber or Millpore pellicon ultrafiltration unit. The concentrate is then treated with a suitable anion exchange resin, such as, for example, DEAE agarose, DEAE cellulose, or QAE agarose, preferably DEAE agarose. The treatment conditions, i.e., a solution of pH about 7–9 and a total salt concentration of approximately 0.01M–0.07M are such that the TNF activity is not adsorbed to the support.

The unbound fractions are then further purified by gel filtration using for example, any commercially available sizing gel such as, for example, Sephadex G-75 Superfine (Pharmacia) which has a molecular weight exclusion of approximately 70,000 daltons. The TNF containing fractions after treatment with the gel are then subjected to SDS PAGE under suitable conditions and the gel slice containing TNF activity is recovered. SDS PAGE is performed according to the method of Laemmli, et al, *Nature* (1970) 227:680 and is a technique well known to those in the art. Variations in specific conditions within suitable ranges are workable and well understood.

The activity-containing fractions from SDS PAGE are then subjected to reverse phase HPLC and eluted with a 0–60% acetonitrile gradient in 0.1% TFA. Other gradient elution systems which are workable include acetic acid and n-propanol.

The human TNF which is thus obtained is sufficiently pure to permit N-terminal amino acid sequencing.

B.3. Isolation of the Coding Sequence mRNA prepared from the HL-60 cells, when added to the standard oocyte translation system, is capable of effecting the production of a TNF factor active in the L-929 cytotoxicity assay. The relative efficacy of oligomeric probes was testable by their ability, when preincubated with this mRNA preparation, to negatively affect TNF production in this translation system ("hybrid arrest"). This criterion can be further refined by radioautography of mRNA gradients hybridized to the kinased probes where the desired TNF encoding mRNA has previously been identified by translation of the fractions in the oocyte system. It was thus possible to decide which of four pools, each containing sixteen 14-mers designed to be complementary to the mRNA, encoding the sequence Asp-Lys-Pro-Val-Ala in the protein, contained the correct sequence. As it was possible to show by Northern blots that even this mixture of sixteen oligomers was not sufficiently specific to hydridize only to TNF-encoding mRNA, these "hydrid arrest" experiments were repeated using eight pairs of 14-mers. One pair was successful in hybridizing the mRNA specifically.

Once a sufficiently specific probe had been identified, it was used to probe a cDNA library formed from the mRNA fraction encoding the desired TNF. Twenty-eight successful hybridizing colonies were picked, plasmid DNA isolated, and several inserts sequenced. A plasmid preparation containing the entire coding sequence, designated pE4, was then used as the source of the coding sequence. An additional plasmid preparation, pB11 was used for mammalian expression.

B.4. Expression of TNF

Nucleotide sequence determination of the pE4 insert permitted, of course, analysis of the location of the coding sequence, and of the available restriction sites in the insert. Although homology was not complete, correct placement could easily be made. For ease in manupulation, it was desired to place an ATG start codon in reading frame and immediately preceding the codon for the N-terminal amino acid of the mature protein sequence, as well as to include a HindIII site immediately upstream of the ATG. This was accomplished by site-directed mutagenesis as is described in detail below. It was then possible to excise the coding sequence with the appropriate start signal in two portions, a HindIII/PstI fragment and a PstI/BamHI fragment, and to insert these fragments into host expression vectors containing control sequences. Alternatively, the entire sequence could be excised as a HindIII fragment. The particular host expression vectors used are pTRP3 which contains a trp promoter upstream of a HindIII site, and a downstream BamHI site; and pFC54.t and pPLOP which contain the $P_L$ promoter similarly disposed.

These expression vectors were transformed into suitable *E. coli* hosts and the resulting transformants cultured under conditions which result in the production of TNF. The TNF can be recovered from the cells by sonication followed by treating the sonicate with a chaotropic agent to solubilize the desired TNF or the sonicate can be assayed directly.

Initial expression has been accomplished in *E. coli;* however, as set forth in greater detail in C.1 below, the coding sequence from pE4 or pB11 could also be ligated to control sequences suitable for expression in other procaryotes, in yeast, in tissue culture, or even in plant cells. Expression in mammalian cells was, in fact, achieved taking advantage of the SV40 promoter of pB11. Choice of the appropriate host will depend on a number of factors, including capability to effect secretion, to effect post-translational processing, and ability to produce high levels of the desired protein under suitable growth conditions.

B.5. Cytotoxic Assay Procedure

The L-929 assay system is an improved convenient in vitro assay which permits rapid measurement of TNF activity. Its degree of correlation with the in vivo tumor necrosis assay of Carswell is, at present, unknown; however, as it utilizes murine tumor cells specifically, the correlation is expected to be high. The protein designated lymphotoxin in EPO publication no. 0100641 (supra) also gives activity in this assay. The assay is similar in concept to that disclosed in U.S. Pat. No. 4,457,916 which used murine L-M cells and methylene blue staining. However, the L-929 assay has been shown to correlate (for HL-60-derived TNF) with human tumor cell line cytotoxicity (See ¶ D.1.b).

In the L-929 assay system herein, L-929 cells are prepared overnight as monolayers in microliter plates. The test samples are diluted 2-fold across the plate, UV irradiated, and then added onto the prepared cell monolayers. The culture media in the wells are then brought to 1 μg/ml actinomycin D. The plates are allowed to incubate 18 hr at 37° C. and the plates are scored visually under the microscope. Each well is given a 25, 50, 75 or 100% mark signifying the extent of cell death in the well. One unit of TNF activity is defined as the reciprocal of the dilution at which 50% killing occurs.

In addition, a more sensitive version of this assay was developed that monitors the release of $^{35}S$ labeled peptides from prelabeled cells, when treated with the test sample and actinomycin D. This version of the assay can be used to quantitate potency, e.g., to evaluate the relative potency of oocyte translated material. Briefly, actively growing L-929 cultures are labeled with $^{35}S$ methionine (200 μCi/ml) for 3 hr in methionine-free media supplemented with 2% dialyzed fetal calf serum. The cells are then washed and plated into 96 well plates, incubated overnight, and treated the next day with 2-fold dilutions of test samples and 1 μg/ml actinomycin D. The cultures were then incubated at 37° C. for 18 hr. 100 μl supernatant aliquots from each well were then transferred onto another 96 well plate, acid (TCA) precipitated, and harvested onto glass fiber filters. The filters wre washed with 95% ethanol, dried and counted. An $NP_{40}$ detergent control is included in every assay to measure maximum release of radioactivity from the cells. The percent $^{35}S$ release is then calculated by the ratio of the difference in count between the treated cells and untreated controls divided by the difference between NP$_{40}$ treated cells and untreated controls, i.e., by the ratio:

$$\% \text{ release} = \frac{\text{sample} - \text{cell control}}{NP_{40} - \text{cell control}} \times 100.$$

Higher TNP potency results in higher values of this ratio.

B.6. Production of TNF Muteins

The invention contemplates a number of modifications of mTNF which are advantageous in obtaining protein of optimal activity. Several specific alterations were made in the primary amino acid sequence which do result in increased specific activity in the assay of ¶ B.5 above. For example, deletion of the first four amino acids from the sequence of mTNF results in a protein of specific activity several fold higher than that of the "native" recombinant protein. Similar N-terminal deletions in the cysteine depleted muteins of mTNF are also expected to enhance activity. It appears that the first ten amino acids may be deleted from the mTNF or corresponding cysteine-depleted muteins without destroying activity. The production of these muteins is effected by subjecting expression vectors containing the coding sequence for mTNF or for its cysteine-depleted analogs to site specific mutagenesis using primers which correspond to the desired deletions. Thus are obtained modified expression vectors with the appropriate changes in the coding sequence. The resulting modified vectors are transformed into suitable hosts, which are then cultured under conditions resulting in the production of the encoded muteins. These muteins are then purified from bacterial culture as was the "native" mTNF protein and shown to have undiminished or enhanced activity.

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

C.1. Hosts and Control Sequences

Procaryotes most frequently are represented by various strains of *E. coil*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al *Nucleic Acids Res* (1980) 8:4057) and the lambda derived P$_L$ promoter and N-gene ribosome binding site (Shimatake, et al, *Nature* (1981) 292:128), which has been made useful as a portable control cassette, as set forth in copending application Ser. No. 578,133, filed Feb. 8, 1984, and assigned to the same assignee. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used although a number of other strains are commonly available. While vectors employing the 2 micron origin of replication are illustrated, Broach, J. R., *Meth Enz* (1983) 101:307, other plasmid vectors suitable for yeast expression are known (see, for example, Stinchcomb, et al, *Nature* (1979) 282:39, Tschempe, et al, *Gene* (1980) 10:157 and Clark, L, et al, *Meth Enz* (1983) 101:300). Control sequences for yeast vectors include promoters for the synthesis of glycolytic enzymes (Hess, et al, *J Adv Enzyme Req* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al, *J Biol Chem* (1981) 256:1385) or the LEU2 gene obtained from YEp13 (Broach, J., et al, *Gene* (1978) 8:121), however any vector containing a yeast compatible promoter, origin of replication and other control sequences is suitable.

It is also, of course, possible to express genes according polypeptides in eucaryotic host cell cultures derived from multicellular organisms. See, for example, *Tissue Cultures*, Academic Press, Cruz and Patterson, editors (1973). Useful host cell lines include VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273:113), or other viral promoters such as those derived from polyoma, Adenovirus 2, bovine papiloma virus, or avian sarcoma viruses. General aspects of mammalian cell host system transformations have been described by Axel; U.S. Pat. No. 4,399,216 issued Aug. 16, 1983. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al, *J Mol Appl Gen* (1982) 1:561) are available.

C.2. Transformations

Depending on the host cell used, transformation is done using standard techniques appropriate to such cells. The calcium treatment employing calcium chloride, as described by Cohen, S. N., *Proc Natl Acad Sci (USA)* (1972) 69:2110, or the RbCl$_2$ method described in Maniatis, et al, *Molecular Cloning: A Laboratory Manual* (1982) Cold Spring Harbor Press, p. 254 was used for procaryotes or other cells which contain substantial cell wall barriers. Infection with *Agrobacterium tumefaciens* (Shaw, C. H., et al, *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al, *J Bact* (1977) 130:946 and Hsiao, C. L., et al, *Proc Natl Acad Sci (USA)* (1979) 76:3829.

C.3. Probing cDNA or Genomic Libraries cDNA or genomic libraries are screened using the colony hybridization procedure. Each microtiter plate is replicated onto duplicate nitrocellulose filter papers (S & S type BA-85) and colonies are allowed to grow at 37° C. for 14–16 hr on L agar containing 50 μg/ml Amp. The colonies are lysed and DNA fixed to the filter by sequential treatment for 5 min with 500 mM NaOH, 1.5M NaCl, and are washed twice for 5 min each time with 5×standard saline citrate (SSC). Filters are air dried and baked at 80° C. for 2 hr. The duplicate filters are prehybridized at 42° C. for 6–8 hr with 10 ml per filter of DNA hybridization buffer (5×SSC, pH 7.0 5×Denhardt's solution (polyvinylpyrrolidine, plus Ficoll and bovine serum albumin; 1× =0.02% of each), 50 mM sodium phosphate buffer at pH 7.0, 0.2% SDS, 20 μg/ml Poly U, and 50 μg/ml denatured salmon sperm DNA).

The samples are hybridized with kinased probe under conditions which depend on the stringency desired. Typical moderately stringent conditions employ a temperature of 42° C. for 24–36 hr with 1–5 ml/filter of DNA hybridization buffer containing probe. For higher stringencies high temperatures and shorter times are employed. The filters are washed four times for 30 min each time at 37° C. with 2×SSC, 0.2% SDS and 50 mM sodium phosphate buffer at pH 7, then are washed twice with 2×SSC and 0.2% SDS, air dried, and are autoradiographed at −70° C. for 2 to 3 days.

C.4. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol followed by running over a Sephadex G-50 spin column. If desired, size separation of the cleaved fragments may be performed by polyacylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA plymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 μM dNTPs. The Klenow fragment fills in at 5′ sticky ends but chews back protruding 3′ single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Metteucci, et al (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl$_2$, 5 mM dithiothreitol, 1–2 mM ATP, 1.7 pmoles γ32P-ATP (2.9 mCi/mmole), 0.1 mM spermidine, 0.1 mM EDTA.

Ligations are performed in 15–30 μl volumes under the following standard conditions and temperatures: 20 mM Tris-Cl pH 7.5, 10 mM MgCl$_2$, 10 mM DTT, 33 μg/ml BSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 μg/ml total DNA concentrations (5–100 nM total end concentration). Intermolecular blunt end ligations (usually employing a 10–30 fold molar excess of linkers) are performed at 1 μM total ends concentration.

In vector construction employing "vector fragments", the vector fragment is commonly treated with bacterial alkaline phosphatase (BAP) in order to remove the 5′ phosphate and prevent religation of the vector. BAP digestions are conducted at pH 8 in approximately 150 mM Tris, in the presence of Na$^+$ and Mg$^{+2}$ using about 1 unit of BAP per μg of vector at 60°

C. for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

C.5. Verification of Construction

In the constructions set forth below, correct ligations for plasmid construction are confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). The isolated DNA is analyzed by restriction and/or sequenced by the dideoxy method of Sanger, F., et al, *Proc Natl Acad Sci (USA)* (1977) 74:5463 as further described by Messing, et al, *Nucleic Acids Res* (1981) 9:309, or by the method of Maxam, et al, *Methods in Enzymology* (1980) 65:499.

C.6. Hosts Exemplified

Host strains used in cloning and expression herein are as follows:

For cloning and sequencing, and for expression of construction under control of most bacterial promoters, *E. coli* strain MM294 (supra), Talmadge, K., et al, *Gene* (1980) 12:235; Meselson, M., et al, *Nature* (1968) 217:1110, was used as the host. For expression under control of the $P_LN_{RBS}$ promoter, *E. coli* strain K12 MC1000 lambda lysogen, $N_7N_{53}cI857SusP_{80}$, ATCC 39531 (hereinafter sometimes referred to as MC1000-39531) is used.

For M13 phage recombinants, *E. coli* strains susceptible to phage infection, such as *E. coli* K12 strain DG98 are employed. The DG98 strain has been deposited with ATCC July 13, 1984 and has accession number 1965.

D. Cloning and Expression of Human TNF

The following illustrates the methods used in obtaining the coding sequence for human TNF-1, for disposing this sequence in expression vectors, and for obtaining expression of the desired protein.

D.1. Preparation and Purification of Human TNF

D.1.a. Induction of TNF

High density ($\geq 2 \times 10^6$ cells/ml) stationary HL-60 cells were centrifuged, washed with RPMI 1640 medium in the absence of serum, and then resuspended at a density of $1 \times 10^7$ cells/ml. The cells were then treated with 100 ng/ml of a phorbol ester, 12-O-tetradecanorylphorbol-13-acetate (TPA) for 30 min at 37° C. in a suspension culture with constant agitation. The cultures were centrifuged, the supernatant was decanted, the cells were resuspended at $1 \times 10^7$ cells/ml in RPMI, containing 10 µg/ml bacterial lipopolysaccharide (LPS) and 10 µM Ca ionophore (A23817) for 4 hr at 37° C. with constant agitation. The cells were spun down at 1200 rpm for 10 min, and the supernatants recentrifuged at 8000 rpm for 20 min. The resulting supernatant was used in the purification scheme of D.1.b to obtain native TNF.

D.1.b. Purification of TNF

About 4–8 liters of the supernatant prepared from induced HL-60 in ¶ D.1.a were concentrated via Amicon hollow fiber (1 square foot cartridge/10,000 MW cutoff) to approximately 300 ml. The concentrated culture fluid was centrifuged to remove cell debris, and supernatant adjusted with 30 mM ammonium bicarbonate buffer (pH 8.2) to a conductance of 6.2 mS. The solution was further concentrated by ultrafiltration using a PM10 (Amicon) membrane, and the concentrated fluid clarified by centrifugation (20,000×g for 10 min).

The supernatant was then applied to a DEAE ion exchange column equilibrated in 30 mM ammonium bicarbonate/1 mM NaCl pH 8.2, and the column washed with the same buffer. Fractions were collected and protein monitored at 280 nm. These unbound fractions were assayed using the L-929 cytotoxicity assay and those having TNF activity pooled and again concentrated by ultrafiltration.

The concentrate was applied to Sephadex G75 Superfine (Pharmacia) equilibrated in 30 mM ammonium bicarbonate buffer (pH 7.4). Unbound fractions obtained by washing with the same buffer were monitored at 280 nm and assayed for TNF. Fractions containing peak TNF bioactivity were lyophilized.

The lyophilized protein was resuspended in Laemmli SDS sample buffer and electrophoresed on SDS-polyacrylamide gel. The gel was sliced into 2 mm sections, and the protein from each section was eluted by immersion in 1 ml of 30 mM ammonium bicarbonate buffer (pH 7.4) and overnight shaking at room temperature.

The sections containing the TNF bioactivity were applied onto a Vydac C-4 reverse phage HPLC column equilibrated in 0.1% trifluoroacetic acid (TFA), and the activity eluted using a linear gradient 0%–60% acetonitrile in 0.1% TFA. Protein was monitored at 280 nm and 214 nm, and the fractions bioassayed after lyophilization and suspended in 30 mM ammonium bicarbonate buffer pH 7.4. Fractions containing TNF activity were again lyophilized.

The resulting protein was of sufficient purity to be useful in sequence analysis. The sequence was determined using a gas phase sequenator (Applied Biosystems Inc.). The sequence obtained from the first 22 amino acids is shown below.

```
 1    2    3    4    5    6    7    8    9
Val—Arg—Ser—Arg—Thr—Pro—Ser—Asp—Lys—

10   11   12   13   14   15   16   17   18
 —Pro—Val—Ala—Val—Ser—Val—Ala—Asn—Pro—

19    20   21   22
                         —(Gln)—(Ala)—Glu—Gly.
```

In addition, the purified protein (from the G-75 gel) was tested with a modification of the L-929 cytotoxicity assay using alternate human tumor and normal cell lines as substrate. The G-75 fractions which were cytotoxic in this assay against L-929 cells were also cytotoxic against Hs939T (a melanoma line) BT-20 (breast carcinoma), A427 (lung carcinoma) HT-1080 (colon carcinoma) and HT-29 (colon carcinoma). These fractions were not cytotoxic against Hs939sk (skin fibroblasts), HeLa cells (cervical carcinoma) Hs27F (foreskin fibroblasts) or COS7 (SV40-transformed monkey cells).

D.2. Preparation of the Coding Sequence

An intronless DNA sequence encoding human TNF was prepared by the procedure herein described. A human promyelocytic leukemia cell line which produces large amounts of TNF when induced, the HL-60 line, obtainable from ATCC, accession no. CCL 240, was used as the source of mRNA to obtain a cDNA library. Using oligomeric probes constructed on the basis of the protein sequence determined from TNF purified from these cells, this cDNA library was probed to retrieve the entire coding sequence for the protein.

D.2.a. Preparation of Enriched mRNA

Total messenger RNA was extracted and purified from HL-60 cells as follows: HL-60 cells were induced for TNF production as set forth in ¶ D.1.a, and the 4-hr cell suspension harvested by centrifugation. Total cytoplasmic ribonucleic acid (RNA) was isolated as follows; all steps are at 4° C. Cells are washed twice in PBS (phosphate buffered saline) and resuspended in IHB (140 mM NaCl, 10 mM Tris, 1.5 mM MgCl$_2$, pH 8) containing 10 mM vanadyl adenosine complex (Berger, S. L., et al, *Biochem* (1979) 18: 5143).

A non-ionic detergent of the ethylene oxide polymer type (NP-40) was added to 0.3% to lyse the cellular, but not nuclear membranes. Nuclei were removed by centrifugation at 1,000×g for 10 min. The post-nuclear supernatant was added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant was re-extracted 4 times and phase separated by centrifugation at 2,000×g for 10 min. The RNA was precipitated by adjusting the sample to 0.25M NaCl, adding 2 volumes of 100% ethanol and storing at −20° C. The RNA was pelleted at 5,000×g for 30 min, washed with 70% and 100% ethanol, and dried. Polyadenylated (Poly A+) messenger RNA (mRNA) was obtained from the total cytoplasmic RNA by chromatography on oligo dT cellulose (Aviv, J., et al, *Proc Natl Acad Sci* (1972) 69: 1408–1412): The RNA was dissolved in ETS (10 mM Tris, 1 mM EDTA, 0.5% SDS, pH 7.5) at a concentration of 2 mg/ml. This solution was heated to 65° C. for 5 min, then quickly chilled to 4° C. After bringing the RNA solution to room temperature, it was adjusted to 0.4M NaCl and slowly passed through an oligo dT cellulose column previously equilibrated with binding buffer (500 mM NaCl, 10 mM Tris, 1 mM EDTA, pH 7.5). The flow-through was passed over the column twice more, and the column washed with 10 volumes of binding buffer. Poly A+ mRNA was eulted with aliquots of ETS, extracted once with TE-saturated phenol chloroform and precipitated by the addition of NaCl to 0.2M and 2 volumes of 100% ethanol. The RNA was reprecipitated twice, washed once in 70% and then in 100% ethanol prior to drying.

The poly A+ mRNA was fractionated on a sucrose gradient in 10 mM Tris-HCl, pH 7.4, 1 mM EDTA, 10 mM NaCl and 0.1% SDS. After centrifugation in a Beckman SW40 rotor at 38,000 rpm for 17 hr, mRNA fractions were recovered from the gradient by ethanol precipitation. The fractions containing TNF mRNA were identified by injecting the mRNA into oocytes and assaying the oocyte extracts for cytotoxic activity. Fractions containing peak activity were pooled for use in cDNA library construction.

D.2.b. Construction of a cDNA Library cDNA was made from the enriched 16S mRNA fraction using oligo dT priming of the poly A tails and AMV reverse transcriptase employing the method of Okayama, H., et al, *Mol Cell Biol* (1983) 3: 280, incorporated herein by reference. This method results in a higher proportion of full length clones and effectively uses as host vector portions of two vectors therein described, and readily obtainable from the authors, pcDV1 and pL1. The resulting vectors contain the insert between vector fragments containing proximal BamHI and XhoI restriction sites; the vector contains the pBR322 origin of replication, and Amp resistance gene.

Other methods of preparing cDNA libraries are, of course, well known in the art. One, now classical, method uses oligo dT primer, reverse transcriptase, tailing of the double stranded cDNA with poly dG, and annealing into a suitable vector, such as pBR322 or a derivative thereof, which has been cleaved at the desired restriction site and tailed with poly dC. A detailed description of this alternate method is found, for example, in U.S. Ser. No. 564,224, filed Dec. 20, 1983, and assigned to the same assignee, incorporated herein by reference.

In the method used here, the enriched mRNA (5 μg) was denatured by treatment with 10 mM methyl mercury at 22° C. for 5 min and detoxified by the addition of 100 mM 2-mercaptoethanol (Payvar, F., et al, *J Biol Chem* (1979) 254: 7636–7642). Plasmid pcDV1 was cleaved with KpnI, tailed with dTTP, and annealed to the denatured mRNA. This oligo dT primed mRNA was treated with reverse transcriptase, and the newly synthesized DNA strand tailed with dCTP. Finally, the unwanted portion of the pcDV1 vector was removed by cleavage with HindIII. Separately, pL1 was cleaved with PstI, tailed with dGTP, cleaved with HindIII, and then mixed with the poly T tailed mRNA/cDNA complex extended by the pcDV1 vector fragment, ligated with *E. coli* ligase and the mixture treated with DNA polymerase I (Klenow) *E. coli* ligase, and RNase H. The resulting vectors are transformed into *E. coli* L12 MM294 to Amp$^R$.

D.2.c. Selection of Probe

Oligomers complementary to the coding sequence for amino acids 8-12 of the purified TNF sequence were prepared. Because of codon redundancy, a total of sixty-four 14-mers are candidates for complementation to the messenger encoding this portion. All sixty-four 14-mers were prepared, and divided into four pools of sixteen. Each pool was mixed with the sucrose gradient size-fractionated enriched mRNA preparation, prepared as above, and the mixture injected into the oocyte translation system. Controls were run using untreated messenger RNA. The proteins produced in the oocyte systems were subjected to L-929 cytotoxicity assay ($^{35}$S release), and the proteins derived from oocytes injected with control and with a mixture of mRNA with three of the oligomer pools shows activity. In this "hybrid arrest" assay, only the oocyte injected with messenger which had been treated with the pool having the sequence was inactive. The specificity of this oligomer pool was further determined using "dot blot" hybridization with enriched mRNA prepared as above from both induced and uninduced HL-60 cells, as well as the corresponding mRNA fraction obtained from cells known to be producers of lymphotoxin. This pool hybridized well to the induced mRNA, but failed to hybridize with the corresponding fractions from the uninduced or lymphotoxin producing cells. However, Northern blots using the kinased pool as probe demonstrated that it contained sequences which cross hybridize with the 18S (ribosomal) RNA fraction and to pBR322 DNA.

The successful pool was therefore further fractionated by synthesizing its members as eight pairs of 14-mers, each of which was used in the "hybrid arrest" assay performed as set forth above. Only the pair with the sequence was successful in inhibiting the synthesis of TNF in the oocytes. Dot blot experiments using the fractionated induced HL-60 mRNA fraction, induced total HL-60 poly A+ RNA, uninduced HL-60 poly A+ RNA, and pBR322 DNA confirmed the specificity of the foregoing 14-mer pair and the inability of the remaining pairs to hybridize to the desired messenger.

D.2.d. Recovery of the Coding Sequence

The cDNA library prepared above was probed with the 14-mer pair identified in D.2.c. Twenty-eight colonies which hybridized with probe were picked, cultured, and the plasmid DNA isolated. Plasmids containing inserts of sufficient length to encode the entire sequence were selected and several were assayed for the correct sequence using hybrid translation in combination with the $^{35}$S release version of the cytotoxic assay, as described in B.5 above. Hybrid translation assays use the test sequence to retrieve the correct mRNA from unfractionated preparations as verified by assaying the protein produced by the oocyte translation system injected with the retrieved messenger.

The plasmid cDNA to be tested is bound to filters, and the filters treated with poly A+ RNA isolated from induced HL-60 cells. The filters are then eluted, and the eluates injected into the oocyte translation system. The oocytes are extracted for protein, which is then tested in the $^{35}$S version of the L-929 cytotoxic assay. The results for several hybridizing clones, designated E2-E4, E6 and E8 are shown below:

| Sample | % Release of $^{35}$S |
|---|---|
| E1 | 7 |
| E2 | 23 |
| E3 | 32 |
| E4 | 33 |
| E6 | 26 |
| E8 | 11 |
| pBR322 | 9 |
| A+ | 34 |
| B+ | 24 |

(A+ and B+ are controls using enriched mRNA as obtained by sucrose gradient; E1 and pBR322 are negative controls.)

Figure 2:
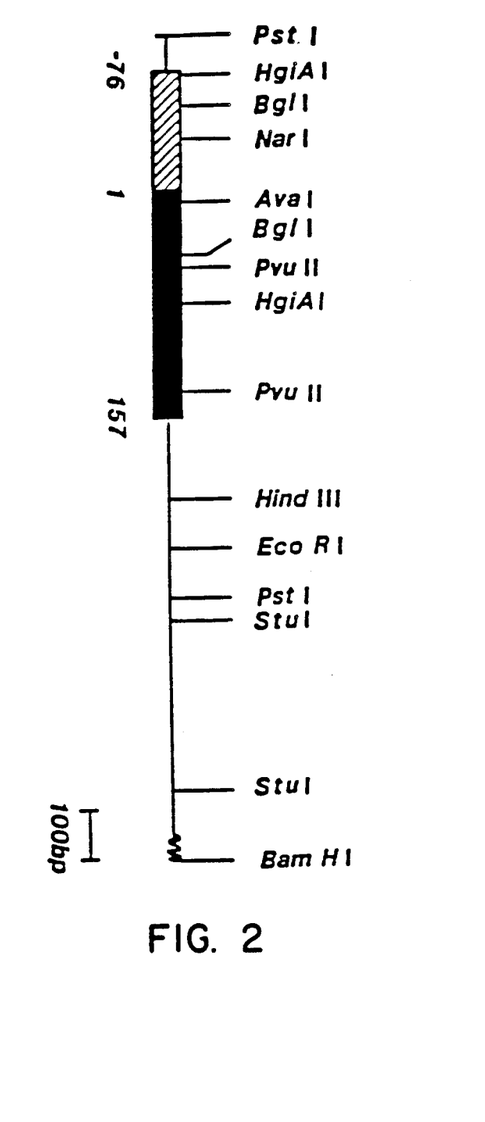
FIG. 2 shows a restriction map of the insert in pE4.

Restriction analysis and partial sequencing of the inserts indicated that two candidate plasmids, pE4 and pB11 were likely to have the complete TNF encoding sequence. The results of this analysis for pE4 are shown in FIG. 2.

pE4 was sequenced and the correct reading frame for TNF identified by matching the amino acid sequence deduced from translation of all three possible reading frames with the known N-terminal sequence of the native mature TNF as determined by N-terminal sequencing of the purified protein (see FIG. 1). The amino acids in the mature protein are numbered starting with the valine at position 1. As noted above, homology was not complete. However, the high degree of homology indicated that the correct cDNA had been chosen. Verification of the experimentally determined restriction cleavage sites shown in FIG. 2 is also provided. The HindIII site upstream of the 3' PstI site in the 1.1 kb PstI fragment is downstream of the stop codon, thus permitting excision of the coding sequence as a HindIII cassette, after modification of the upstream region as described below.

D.3. Characteristics of Human TNF as Determined from the DNA Sequence

As deduced from the cDNA sequence set forth in FIG. 1, the mature TNF protein contains 157 amino acid residues, and has a molecular weight, without glycosylation, of approximately 17,354. The leader sequence apparently contains roughly 76 amino acids, beginning with the first available Met start codon. There are 2 cysteine residues, at positions 69 and 101, leading to the possibility that the active structure contains a disulfide link.

D.4. Preparation of Expression Vectors

D.4.a. Modification of the N-terminal Codons

It was convenient, in effecting the expression of the mature protein, to introduce an ATG start codon immediately preceding the GTC sequence encoding N-terminal valine of the mature protein (designated 1 in FIG.

1), as well as to provide a HindIII site immediately upstream of the ATC for ligation into suitable host expression vectors. This was accomplished by site-directed mutagenesis as has been described in ¶ C.4.

In more detail, the DNA fragment containing the upstream portion of the coding sequence was excised from pE4 by digestion with PstI, isolated by agarose gel electrophoresis, recovered by electroelution, and ligated into the PstI site of bacteriophage M13mp18.

The ligated phage were transduced into frozen competent *E. coli* K12 strain DG98 (ATCC #39768) and cultured by plating on media containing $5 \times 10^{-4}$M isopropyl thiogalactoside (IPTG) obtained from Sigma Chem. (St. Louis, MO) and 40 µg/ml X-gal. Non α-complementing white plaques were picked onto fresh media. Mini-cultures were screened for recombinant single strand phage DNA containing inserts of the expected (1.1 kb) size. The structure of the desired recombinant phage, designated clone 4.1, was confirmed using restriction analysis.

A chemically synthesized, purified, 33-mer oligodeoxyribonucleotide having the sequence:

5'-GAAGATGATCTGAC-
CATAAGCTTTGCCTGGGCC-3' was used to introduce a HindIII restriction enzyme site and an ATG-initiation codon before the GTC codon coding for the first amino acid (valine) of the mature TNF protein.

Ten picomoles of the oligonucleotide were hybridized to 2.6 µg of ss clone 4.1 DNA in 15 µl of a mixture containing 100 mM NaCl, 20 mM Tris-HCl, pH 7.9, 20 mM MgCl$_2$ and 20 mM β-mercaptoethanol, by heating at 67° C. for 5 min and 42° C. for 25 min. The annealed mixtures were chilled on ice and then adjusted to a final volume of 25 µl of a reaction mixture containing 0.5 mM of each dNTP, 17 mM Tris-HCl, pH 7.9, 17 mM MgCl$_2$, 83 mM NaCl, 17 mM β-mercaptoethanol, 5 units of DNA polymerase I Klenow fragment, incubated at 37° C. for 1 hr. The reactions were terminated by heating to 80° C. and the reaction mixtures used to transform competent DG98 cells, plated into agar plates and incubated overnight to obtain plage plaques.

Plates containing mutagenized clone 4.1 plaques as well as 2 plates containing unmutagenized clone 4.1 phage plaques, were chilled to 4° C. and phage plaques from each plate were transferred onto 2 nitrocellulose filter circles by layering a dry filter on the agar plate for 5 min for the first filter and 15 min for the second filter. The filters were then placed on thick filter papers soaked in 0.2N NaOH, 1.5M NaCl and 0.2% Triton X-100 for 5 min, and neutralized by layering onto filter papers soaked with 0.5M Tris-HCl, pH 7.5, and 1.5M NaCl for another 5 min. The filters were washed in a similar fashion twice on filters soaked in $2 \times$SSC, dried and then baked in a vacuum oven at 80° C. for 2 hr. The duplicate filters were pre-hybridized at 42° C. for 4 hr with 10 ml per filter of DNA hybridization buffer ($5 \times$SSC, pH 7.0, $4 \times$Denhardts solution (polyvinylpyrrolidine, ficoll and bovin serum albumin, $1 \times = 0.02\%$ of each), 0.1% SDS, 50 mM sodium phosphate buffer, pH 7.0 and 100 µg/nl of denatured salmon sperm DNA. $^{32}$P-labeled probes were prepared by kinasing the primer with labeled ATP. The filters were hybridized to $5 \times 10^6$ cpm/ml of $^{32}$P-labeled primer in 1–5 ml per filter of DNA hybridization buffer at 64° C. for 8 hr.

The filters were washed once at room temperature for 10 min in 0.1% SDS, 20 mM sodium phosphate (buffer) and $6 \times$SSC; once at 37° C. for 20 min in buffer and $2 \times$SSC; once at 50° C. for 20 min in buffer and $2 \times$SSC; and finally at 60° C. for 20 min in buffer and $1 \times$SSC. The filters were air dried and autoradiographed at −70° C. for 4 hr.

Since the oligonucleotide primer was designed to create a new HindIII restriction site in the mutagenized clones, RF-DNA from a number of the clones which hybridized with the primer were digested with this restriction enzyme. One of the mutagenized clone 4.1 plaques which has a new HindIII restriciton site (M13-AW701) was picked and inoculated into a culture of DG98, ssDNA was prepared from the culture supernatant and dsRF-DNA was prepared from the cell pellet. The correct sequence is confirmed by dideoxy sequencing.

The correctly synthesized strands were isolated and cleaved with PstI and HindIII (partial) or with HindIII alone for ligation into expression vectors.

D.4.b. Construction of Expression Vectors

For procaryotic expression, the coding sequence (along with some 3' untranslated nucleotides) was excised from dsM13-AW701 in two ways:

In the first method, the dsM13-AW701 was digested with PstI and then digested partially with HindIII to obtain the HindIII-PstI TNF coding sequence. (Partial HindIII digestion is required because there are several HindIII sites in M13-AW701.). The partial digestion of the DNA fragment can be accomplished by using one-tenth the amount of restriction enzyme required for complete digestion of the DNA. The mixture was incubated at the appropriate temperature for the enzyme and aliquots of the digestion mixture were removed at 10 min intervals for up to 1 hr. The aliquots were then loaded onto a gel and the DNA fragments analyzed. The time point that provided the highest yield of the DNA fragment needed was chosen for a preparative digestion with the restriction enzyme and the appropriate fragment purified from the gel by electroelution.

The PstI/BamHI fragment containing the 3'-noncoding sequence of the TNF gene (see FIG. 2) was purified from pE4 following digestion of the DNA with the enzymes PstI and BamHI.

Together, the HindIII/PstI and PstI/BamHI fragments comprise the coding sequence plus a 600 bp 3' untranslated portion of DNA. The two fragments were ligated into HindIII/BamHI digested host vector pTRP3 as follows:

pTRP3 (see below), contains the *E. coli* trp promoter and ribosome binding site. pTRP3 was digested with HindIII and BamHI, and the vector fragment purified on agarose gel. The isolated fragment was then ligated with the above HindIII/PstI and PstI/BamHI segments in a 3-way ligation, and the mixture used to transform *E. coli* MM294 to Amp$^R$, giving pAW701.

In a second method, dsM13-AW701 was digested with HindIII and the fragment containing the gene isolated on agarose gel. The isolated fragment was ligated with HindIII cleaved, BAPped pTRP3, and transformed into *E. coli* MM294 to obtain pAW702.

pFC54.t (ATCC 39789), containing the P$_L$ promoter and bacillus positive retroregulatory sequence or pPLOP (see below) can also be used as host vectors. These vectors are digested with HindIII and BamHI and the large plasmid fragments containing the control sequences purified on agarose gel. The HindIII/PstI and PstI/BamHI portions of the TNF gene, prepared as set forth above, are ligated, in a three way ligation, into the HindIII and BamHI sites of these vectors resulting in plasmids pAW711 and pAW712 respectively.

Alternatively, the purified HindIII fragment from pE4 is ligated into HindIII cleaved, BAPped pFC54.t or pPLOP to give pAW713 and pAW714, respectively.

D.4.c. Expression of TNF in Procaryotic Hosts pAW701 and pAW702 were transferred into *E. coli* MM294 and the cultures grown under conditions which suppress the trp promoter. Upon induction by tryptophan depletion, production of TNF was initiated. In an analogous fashion, pAW711 was constructed and transferred into *E. coli* MC1000-39531, and the cells were induced by high temerature. After several hours of culturing under induction conditions, the cells were sonicated and the sonicates verified to contain TNF by the L-929 cytotoxicity assay. The results are:

| Plasmid | U/ml |
|---|---|
| 701 | $1.3 \times 10^4$ |
| 702 | $1.3 \times 10^4$ |
| 711 | $2 \times 10^5$ |

Units of TNF activity are as defined in ¶ B.5.

D.4.d Expression of TNF in Eucaryotic Hosts

The vector pB11 isolated from the cDNA library in ¶ D.2.d above, contains the SV40 promoter in operable linkage to the TNF coding sequence. All of the 28 positively hybridizing colonies would be expected to contain this linkage, including, specifically pE4 and pB11, and are thus capable of expression in suitable mammalian hosts. Accordingly, pB11 was used to transform COS-7 monkey kidney cells, and the cells cultured under conditions which effect the induction of the SV40 promoter. As the signal sequence is still present in pB11, and functions in mammalian cell systems, the TNF was secreted into the medium. TNF was assayed in the supernatant above the monolayered COS-7 cells by $^{35}S$ release from L-929 cells, with results as follows:

| Plasmid | $^{35}S$ Release (cpm) |
|---|---|
| B11 | 22,763 |
| E9 (neg control) | 2,739 |
| —DNA | 2,565 |

D.5. Characterization of Recombinant TNF

D.5.a. Purification

*E. coli* DG95 transformed with pAW711 were grown at 37° C. in standard growth medium to an $OD_{600}$ of about 0.5 and then induced by increasing the temperature to 42° C. After 2 hr, the cells were sonicated and the sonicate verified to contain TNF activity using the L-929 cytotoxicity assay (supra). The sonicate was then applied to a DEAE Sepharose column (Pharmacia) and washed with buffer (10 mM Tris, pH 8.2, 1 mM NaCl). Stepwise elution wth 0.02M, 0.04M, 0.1M, and 0.8M NaCl in 10 mM Tris, pH 8.2 yielded fractions containing TNF activity.

Most of the TNF activity eluted at 0.04M NaCl. These fractions were concentrated by ultrafiltration, and then further purified by HPLC using a phenyl TSK-5PW column (LKB). The TNF protein was bound to the column in the presence of 1.8M ammonium sulfate in 0.1M sodium phosphate, pH 7.0, and remained adsorbed when the column is developed by reducing the ammonium sulfate concentration to zero. However, the TNF is eluted using reverse gradient elution from 0.1M sodium phosphate, pH 7, to deionized water. Most of the TNF activity elutes at about 0.02M sodium phosphate. The fractions containing TNF were concentrated by ultrafiltration and applied to a GH25 sizing column (Amicon) to obtain pure TNF.

D.5.b. Separation of TNF Muteins

Isoelectric focusing showed the TNF prepared as set forth in the above paragraph to consist of several species of differing pI values in the range of 5.8–6.8. Two major species were shown to be the expected mature TNF (mTNF) of pI 6.8 and the mutein form (V4TNF), pI 5.8. The results of isoelectric focusing gel show several species of TNF to be present.

To separate mTNF from V4TNF on a preparative scale, the DEAE Sepharose column described in ¶ D.5.a was eluted using a higher degree of fractionation, resulting in a fraction enriched in V4TNF at approximately 0.03M NaCl, before the elution of the major mTNF peak. The enriched V4TNF fraction was concentrated and applied to the phenyl TSK-5PW column for HPLC under the conditions described above. HPLC of the enriched fraction results in a peak containing mTNF at approximately 0.02M phosphate as above described, and the purified V4TNF which elutes with deionized water. The V4TNF peak fractions were concentrated and further purified on GH25 as described above to obtain homogeneous V4TNF, as shown by isoelectric focusing on gels.

D.5.c. Comparison of mTNF and V4TNF

The amino acid compositions of the two TNF species were compared with the results shown below.

| Amino Acid | Predicted composition (cDNA) | $TNF_1$ pI 6.8 | $TNF_2$ pI 5.8 | Difference $TNF_1-TNF_2$ |
|---|---|---|---|---|
| Asx | 12 | 12.7 | 12.4 | 0.3 |
| Thr | 6 | 6.2 | 6.1 | 0.1 |
| Ser | 13 | 12.6 | 10.9 | 1.7 |
| Glx | 20 | 20.5 | 20.2 | 0.3 |
| Pro | 10 | 10.1 | 10.3 | −0.2 |
| Gly | 11 | 11.1 | 11.1 | 0.0 |
| Ala | 13 | 13.4 | 13.1 | 0.3 |
| Val | 13 | 10.9 | 10.2 | 0.7 |
| Met | 0 | 0.2 | 0 | 0.2 |
| Ile | 8 | 6.5 | 6.6 | −0.1 |
| Leu | 17 | 18.7 | 18.5 | 0.2 |
| Tyr | 7 | 6.9 | 7.0 | −0.1 |
| Phe | 4 | 4.0 | 4.0 | 0.0 |
| Lys | 6 | 6.1 | 6.2 | −0.1 |
| His | 3 | 3.0 | 3.0 | 0.0 |
| Arg | 9 | 9.0 | 8.0 | 1.0 |
| n = | 152 | 151.9 | 147.4 | 4.5 |

Both proteins compared in composition reasonably well with the composition predicted from the cDNA sequence; however the ∇4TNF appeared to be lacking 2 serine, 1 valine, and 1 arginine residue. The deletion of these residues from N-terminal sequence was verified by sequencing the ∇4TNF on an automatic protein sequencer which gave a sequence for the first 10 amino acids as:

Ser-Arg-Thr-Pro-Ser-Asp-Lys-Pro-Val-Ala.

Comparison of this sequence with the deduced amino acid sequence in FIG. 1 shows this protein to lack the first 4 amino terminal residues, Val-Arg-Ser-Ser, but to have an N-terminal sequence consistent with the subsequent positions.

The specific activity of fractions across the ∇4TNF peaks obtained from the GH25 purification step set forth above, as identified by absorbance at 280 nm, was tested for specific activity, with the following results:

| Fraction Number | Protein Concentration mg/ml | Bioactivity U/ml | Specific Activity U/mg |
|---|---|---|---|
| 16 | 0.043 | $4.7 \times 10^6$ | $1.1 \times 10^8$ |
| 17 | 0.091 | $1.9 \times 10^7$ | $2.1 \times 10^8$ |
| 18 | 0.102 | $1.4 \times 10^7$ | $1.4 \times 10^8$ |
| 19 | 0.063 | $7.0 \times 10^6$ | $1.1 \times 10^8$ |
| 20 | 0.035 | $2.4 \times 10^6$ | $6.9 \times 10^7$ |

The average specific activity, which is consistent across the peak as predicted for a pure protein, is $1.3 \times 10^8$ U/mg. This is approximately 10-fold higher than that for mTNF.

D.6. Expression of ∇4TNF by *E. coli*

An expression vector encoding ∇4TNF was prepared from pAW711 (supra). pAW711 was digested with HindIII to excise the entire coding sequence for mTNF, and this sequence was isolated by agarose gel electrophoresis, recovered by electroelution, and ligated into the HindIII site of bacteriophage M13mp18.

The ligated phage were transduced into frozen competent *E. coli* K12 strain DG98 (ATCC no. 39768) and cultured by plating on media containing $5 \times 10^{-4}$M isopropyl thiogalactoside (IPTG) obtained from Sigma (St. Louis, MO) and 40 µg/ml X-gal. Non α-complementing white plaques were picked onto fresh media. Mini-cultures were screened for recombinant single strand phage DNA containing inserts of the expected (0.6 kb) size. The structure of the desired recombinant phage, designated clone M13-AW711, was confirmed using restriction analysis.

A chemically synthesized, purified, 35-mer oligodeoxyribonucleotide having the sequence:

5'-CACTCGGGGTT-
CGAGACATAAGCTTTGCCTGGGCC-3' was used to loop out and thereby delete the 12 nucleotides encoding the 4 N-terminal amino acids downstream from the methionine initiation codon.

Ten picomoles of the oligonucleotide were hybridized to 2.6 µg of ss clone M13-AW711 DNA in 15 µl of a mixture containing 100 mM NaCl, 20 mM Tris-HCl, pH 7.9, 20 mM MgCl₂ and 20 mM β-mercaptoethanol, by heating at 67° C. for 5 min and 42° C. for 25 min. The annealed mixtures were chilled on ice and then adjusted to a final volume of 25 µl of a reaction mixture containing 0.5 mM of each dNTP, 17 mM Tris-HCl, pH 7.9, 17 mM MgCl₂, 83 mM NaCl, 17 mM β-mercaptoethanol, 5 units of DNA polymerase I Klenow fragment, incubated at 37° C. for 1 hr. The reactions were terminated by heating to 80° C. and the reaction mixtures used to transform competent DG98 cells, plated onto agar plates and incubated overnight to obtain phage plaques.

Plates containing mutagenized clone M13-AW711 plaques as well as 2 plates containing unmutagenized clone M13-AW711 phage plaques, were chilled to 4° C. and phage plaques from each plate were transferred onto 2 nitrocellulose filter circles by layering a dry filter on the agar plate for 5 min for the first filter and 15 min for the second filter. The filters were then placed on thick filter papers soaked in 0.2 N NaOH, 1.5M NaCl and 0.2% Triton X-100 for 5 min, and neutralized by layering onto filter papers soaked with 0.5M Tris-HCl, pH 7.5, and 1.5M NaCl for another 5 min. The filters were washed in a similar fashion twice on filters soaked in 2×SSC, dried and then baked in a vacuum oven at 80° C. for 2 hr. The duplicate filters were pre-hybridized at 42° C. for 4 hr with 10 ml per filter of DNA hybridization buffer (5×SSC, pH 7.0, 4×Denhardts solution (polyvinylpyrrolidine, ficoll and bovin serum albumin, 1×=0.02% of each), 0.1% SDS, 50 mM sodium phosphate buffer, pH 7.0 and 100 µg/ml of denatured salmon sperm DNA. $^{32}$P-labeled probes were prepared by kinasing the primer with labeled ATP. The filters were hybridized to $5 \times 10^6$ cpm/ml of $^{32}$P-labeled primer in 1-5 per filter of DNA hybridization buffer at 64° C. for 8 hr.

The filters were washed once at room temperature for 10 min in 0.1% SDS, 20 mM sodium phosphate (buffer) and 6×SSC; once at 37° C. for 20 min in buffer and 2×SSC; once at 50° C. for 20 min in buffer and 2×SSC; and finally at 60° C. for 20 min in buffer and 1×SSC. The filters were air dried and autoradiographed at −70° C. for 4 hr. RF-DNAs from positive clones were digested with HindIII, and the fragment containing the mutagenized TNF coding sequence was isolated by gel electrophoresis. The recovered sequence was ligated into HindIII cleaved, BAPed pPLOP to obtain pAW736. The presence of the 12 nucleotide deletion was confirmed by restriction analysis with HindIII and PvuII; pAW736 contains a 134 bp HindIII/PvuII fragment as compared to the 146 bp HindIII/PvuII fragment produced by pAW711. pAW736 was deposited with ATCC on Apr. 10, 1985 and has accession no. 53092.

*E. coli* DG95 transformed with pAW736 were grown and induced as described above. Sonicate was prepared as described above, and aliquots were analyzed using 12% SDS-PAGE. The ∇4TNF protein was purified from the sonicate exactly as described previously, and shown to be identical with the previously prepared ∇4TNF by isoelectric focusing. The isolated ∇4TNF was tested using the L-929 cytotoxicity assay and shown to have a specific activity of approximately $2 \times 10^8$ U/mg.

D.7. Additional N-terminal Deletion Muteins of TNF

In a manner precisely similar to that set forth in ¶ D.6 above, expression vectors were prepared for TNF deletion muteins lacking the first 7 amino terminal residues and the first 5, 6, and 8 amino terminal residues, which vectors were designated pAW737, pAW738, pAW739, and pAW740 respectively. When these vectors were transformed into *E. coli* DG95, and the resulting transformants cultured and induced, the muteins ∇7TNF, ∇5TNF, ∇6TNF and ∇8TNF, respectively, were produced. These muteins showed specific activities several fold higher than mTNF.

In addition, in a precisely corresponding manner, the DNA sequence encoding a cysteine-69 depleted TNF mutein is modified to obtain the analogous N-terminal deleted muteins, ∇4ser₆₉TNF, ∇7ser₆₉TNF, and ∇5ser69TNF, ∇6ser69TNF, and ∇8ser69TNF. (The subscripted number refers to the position of the residue as shown in FIG. 1.) The expression vectors for these muteins are constructed exactly as described in the preceeding paragraphs except substituting for pAW711, in the mutagenesis reaction, the plasmid pAW731 containing the coding sequence for Ser69TNF. pAW731 is extensively described in U.S. Ser. No. 698,939, filed Feb. 7, 1985, incorporated herein by reference and has been deposited at ATCC on Jan. 25, 1985 with accession no. 53007. The expression vectors thus obtained are transformed into *E. coli* and the cells cultured and induced as above to produce the desired proteins. The resulting TNF muteins are comparably active to mTNF.

D.8. Construction of pPLOP pPLOP was deposited at ATCC on Dec. 18, 1984 and has accession no. 39947. Its construction is described below.

D.8.a. Origin of Replication pCS3 provides an origin or replication which confers high copy number of the pPLOP host vector at high temperatures. Its construction is described extensively in U.S. Ser. No. 541,948, filed Oct. 14, 1983, incorporated herein by reference. pCS3 was deposited June 3, 1982 and assigned ATCC number 39142.

pCS3 is derived from pEW27 and pOP9. pEW27 is described by E. M. Wong, *Proc Natl Acad Sci (USA)* (1982) 79: 3570. It contains mutations near its origin of replication which provide for temperature regulation of copy number. As a result of these mutations replication occurs in high copy number at high temperatures, but at low copy number at lower temperatures.

pOP9 is a high copy number plasmid at all temperatures which was constructed by inserting into pBR322 the EcoRI/PvuII origin containing fragment from Col El type plasmid pOP6 (Gelfand, D., et al, *Proc Natl Acad Sci (USA)* (1978) 75: 569). Before insertion, this fragment was modified as follows: 50 μg of pOP6 was digested to completion with 20 units each BamHI and SstI. In order to eliminate the SstI 3′ protruding ends and "fill in" the BamHI 5′ ends, the digested pOP6 DNA was treated with *E. coli* DNA polymerase I (Klenow) in a two-stage reaction first at 20° C. for elimination of the 3′ SstI protruding end and then at 9° C. for repair at the 5′ end. The blunt ended fragment was digested and 0.02 pmole used to transform competent DG75 (O'Farrell, P., et al, *J Bacteriology* (1978) 134: 645–654). Transformants were selected on L plates containing 50 μg/ml ampicillin and screened for a 3.3 kb deletion, loss of an SstI site, and presence of a newly formed BamHI site.

One candidate, designated pOP7, was chosen and the BamHI site deleted by digesting 25 μg of pOP7 with 20 units BamHI, repairing with *E. coli* DNA polymerase I fragment (Klenow), and religating with T4 DNA ligase. Competent DG75 was treated with 0.1 μg of the DNA and transformants selected on L plates containing 50 μg/ml ampicillin. Candidates were screened for the loss of the BamHI restriction site. pOP8 was selected. To obtain pOP9 the AvaI(repaired)/EcoRI Tet$^R$ fragment from pBR322 was prepared and isolated and ligated to the isolated PvuII(partial)/EcoRI 3560 bp fragment from pOP8.

Ligation of 1.42 kb EcoRI/AvaI(repair) Tet$^R$ (fragment A) and 3.56 kb EcoRI/PvuII Amp$^R$ (fragment B) used 0.5 μg of fragment B and 4.5 μg of fragment A in a two-stage reaction in order to favor intermolecular ligation of the EcoRI ends.

Competent DG75 was transformed with 5 μl of the ligation mixture, and transformants were selected on ampicillin (50 μg/ml) containing plates. pOP9, isolated from Amp$^R$Tet$^R$ transformants showed high copy number, colicin resistance, single restriction sites for EcoRI, BamHI, PvuII, HindIII, 2 restriction sites for HincII, and the appropriate size and HaeIII digestion pattern.

To obtain pCS3, 50 μg pEW27 DNA was digested to completion with PvuII and the EcoRI. Similarly, 50 μg of pOP9 was digested to completion with PvuII and EcoRI and the 3.3 kb fragment was isolated.

0.36 μg (0.327 pmoles) pEW27 fragment and 0.35 μg (0.16 pmoles) pOP9 fragment were ligated and used to transform *E. coli* MM294. Amp$^R$Tet$^R$ transformants were selected. Successful colonies were initially screened at 30° C. and 41° C. on beta-lactamase assay plate and then for plasmid DNA levels following growth at 30° C. and 41° C. A successful candidate, designated pCS3, was confirmed by sequencing.

D.8.b. Preparation of the $P_LN_{RBS}$ Insert

The DNA sequence containing $P_L$ phage promoter and the ribosome binding site for the N-gene ($N_{RBS}$) was obtained from pFC5, and ultimately from a derivative of pKC30 described by Shimatake and Rosenberg, *Nature* (1981) 292: 128. pKC30 contains a 2.34 kb fragment from lambda phage cloned into the HindIII/-BamHI vector fragment from pBR322. The $P_L$ promotor and $N_{RBS}$ occupy a segment in pKC30 between a BglII and HpaI site. The derivative of pKC30 has the BglII site converted to an EcoRI site.

BglII site immediately preceding the $P_L$ promoter was converted into an EcoRI site as follows: pKC30 was digested with BglII, repaired with Klenow and dNTPs and ligated with T4 ligase to an EcoRI linker (available from New England Biolabs) and transformed into *E. Coli* K12 strain MM294 Lambda+. Plasmids were isolated from Amp$^R$Tet$^S$ transformants and the desired sequence confirmed by restriction analysis and sequencing. The resulting plasmid, pFC3, was double-digested with PvuI and HpaI to obtain an approximately 540 bp fragment isolated and treated with Klenow and dATP, followed by S1 nuclease, to generate a blunt ended fragment with the 3′ terminal sequence -AGGAGAA where the -AGGAGA portion is the $N_{RBS}$. This fragment was restricted with EcoRI to give a 347 base pair DNA fragment with 5′-EcoRI (sticky) and HinfI (partial repair, S1 blunt)-3′ termini.

To complete pFC5, pβI-Z15 was used to create a HindIII site 3′ of the $N_{RBS}$. pβI-Z15 was deposited Jan. 13, 1984, ATCC No. 39578, and was prepared by fusing a sequence containing ATG plus 140 bp of β-IFN fused to lac Z into pBR322. In pβI-Z15, the EcoRI site of pBR322 is retained, and the insert contains a HindIII site immediately preceding the ATG start codon of β-IFN. pβI-Z15 was restricted with HinIII, repaired with Klenow and dNTPs, and then digested with EcoRI. The resulting EcoRI/HindIII (repaired) vector fragment was ligated with the EcoRI/HinfI (repaired) fragment above, and the ligation mixture used to transform MC10000-39531. Transformants containing the successful construction were identified by ability to grow on lactose minimal plates at 34° but not at 30°. (Transformations were plated on X-gal-Amp plates at 30° and 34° and minimal-lactose plates at 30° and 34°.

Transformants with the proper construction are blue on X-gal-Amp plates at both temperatures, but on minimal lactose plates, grow only at 34°.) The successful construct was designated pFC5.

D.8.c. Completion of pPLOP pCS3 was then modified to provide the $P_L$ and $N_{RBS}$ control sequences. pCS3 was digested with HindIII, and then digested with EcoRI. The vector fragment was ligated with an isolated EcoRI/HindIII from pFC5 containing the $P_L N_{RBS}$ and transformed into *E. coli* MM294. The correct construction of isolated plasmid DNA was confirmed by restriction analysis and sequencing and the plasmid designated pPLOP.

D.9. Construction of pTRP3 pTRP3 was deposited with ATCC on Dec. 18, 11984 and has accesion no. 39946. Its construction is as follows:

To construct the host vector containing the trp control sequences behind a HindIII site, the trp promoter/operator/ribosome binding site sequence, lacking the attenuator region, was obtained from pVH153, obtained from C. Yanofsky, Stanford University. Trp sequences are available in a variety of plasmids well known in the art. pVH153 was treated wih HhaI (which cuts leaving an exposed 3' sticky end just 5' of the trp promoter) blunt-ended with Klenow, and partially digested with TaqI. The 99 bp fragment corresponding to restriction at the TaqI site, 6 nucleotides preceding the ATG start codon of trp leader was isolated, and then ligated to EcoRI(repair)/ClaI digested, pBR322 to provide pTRP3.

On Oct. 15, 1984, Applicants have deposited with the American Type Culture Collection, Rockvill, MD, USA (ATCC) the plasmid pE4, described hererin, ATCC accession no. 39,894. On Nov. 8, 1984, pAW711 was deposited and given ATCC accession No. 39918. Plasmid pAW736 was deposited at ATCC on Apr. 10, 1985 and has accession no. 53092. These deposits were made under the provisions of the Budapest Treaty on the International Recognition of the Deposit of Microorganisms for the Purposes of Patent Procedure and the Regulations thereunder (Budapest Treaty). This assures maintenance of a viable culture for 30 years from the date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any governement in accordance with its patent laws.

We claim:

1. Human tumor necrosis factor (TNF) which is ∇4-mTNF.

2. A recombinant DNA sequence which encodes ∇4-mTNF.

3. The DNA of claim 2 which is uninterrupted by introns.

4. A recombinant DNA having a DNA sequence encoding ∇4-mTNF, operably linked to appropriate regulatory control sequences which are capable of effecting the expression of said coding sequences in transformed cells.

5. Recombinant host cells transformed with the DNA of claim 4.

6. The cells of claim 5 which are procaryotic cells.

7. The cells of claim 5 which are mammalian cells.

8. Human ∇4-mTNF produced by the cells of claim 5.

9. A method for producing human ∇4-mTNF which comprises culturing recombinant host cells wherein a recombinant DNA transformed in said host cells has a DNA sequence encoding ∇4-mTNF, operably linked to appropriate regulatory control sequence which are capable of effecting the expression of said coding sequences in said transformed cells.

10. A recombinant vector capable of expression in procaryotic cells which comprises a DNA sequence encoding ∇4-mTNF operably linked to control sequences compatible with said procaryotic cells.

11. Recombinant procaryotic cells transformed with the vector of claim 10.

12. The vector of claim 11 which is pAW736.

13. The recombinant DNA of claim 10 which includes a lambda derived $P_L$ promoter.

14. The recombinant DNA of claim 13 wherein the recombinant DNA includes an N-gene ribosome binding site.

* * * * *